United States Patent [19]

Murphy et al.

[11] Patent Number: 4,865,831
[45] Date of Patent: Sep. 12, 1989

[54] RECOVERY OF ZINC AND AMMONIUM CHLORIDE

[75] Inventors: Frank H. Murphy, Alvin; Matt W. Oleksy, Nederland, both of Tex.

[73] Assignee: The Dow Chemical Company, Midland, Mich.

[21] Appl. No.: 160,880

[22] Filed: Feb. 26, 1988

[51] Int. Cl.$^4$ ................ C01G 9/00; C01G 9/04
[52] U.S. Cl. ................ 423/463; 423/101
[58] Field of Search ........... 423/101, 103, 104, 471, 423/463

[56] References Cited

U.S. PATENT DOCUMENTS

| | | | |
|---|---|---|---|
| 2,012,809 | 2/1932 | Derick | 423/463 |
| 2,145,817 | 4/1937 | Stoops | 423/463 |
| 2,288,405 | 2/1940 | Kepfer | 423/463 |
| 3,967,957 | 7/1976 | Fonseca | 423/150 |
| 4,500,498 | 2/1985 | Kruesi et al. | 423/100 |
| 4,703,123 | 10/1987 | Murphy | 546/345 |

FOREIGN PATENT DOCUMENTS 1206901  9/1970  United Kingdom ........... 423/463

OTHER PUBLICATIONS

Sutherland, M. M. J., *A Text-Book of Inorganic Chemistry*, vol. X, The Metal-Ammines, London, 1928, pp. 47-48.

O. Erametsa et al., Soumen Kemistilehti, B 39(12), pp. 277-280, (1966, (Chem. Abs. 67, 94805z, (1967)).

N. C. Cahoon, Trans. Electrochem. Soc., 92, p. 7 (1947), (Chem. Abs., 42, 43a (1948)).

*Primary Examiner*—Robert L. Stoll
*Attorney, Agent, or Firm*—D. Wendell Osborne

[57] ABSTRACT

The zinc and ammonia values in solutions containing zinc chloride or zinc monoammine chloride and ammonium chloride can be recovered by adding ammonia to a pH of about 5.5 to about 8.5 and separating the precipitated zinc diammine chloride from the residual aqueous solution of ammonium chloride. The zinc diammine chloride can be used as is or further converted to anhydrous zinc chloride and ammonia and the aqueous solution of ammonium chloride can be used as is or basified to recover the ammonia.

14 Claims, No Drawings

RECOVERY OF ZINC AND AMMONIUM CHLORIDE

BACKGROUND OF THE INVENTION

The present invention relates to a process for the recovery of zinc and ammonia values from aqueous solutions containing zinc chloride or zinc monoammine chloride and ammonium chloride. It is particularly well suited to the recovery of the zinc and ammonia values from the aqueous by-product streams obtained in the reduction of organochlorine compounds with zinc in the presence of ammonium chloride.

Because of their high cost, the use of zinc metal and zinc chloride as reagents in the manufacture of organic materials is generally feasible only when methods are available to recover the zinc values contained in the aqueous by-product steams produced. Recovery in the form of an aqueous solution of zinc chloride is common since such a solution can be used directly or as a raw material for the production of other zinc compounds. The presence of additional substances, such as ammonium chloride, in by-product streams or other aqueous zinc chloride-containing solutions from which recovery is desired, however, makes the recovery of zinc products in sufficiently pure form to be useful difficult. New, low cost methods of recovery are of great interest. The recovery of ammonia values is also of interest since any ammonia values not recovered represents both a loss of assets and a waste disposal problem.

It has been disclosed in U.S. Pat. 4,500,498 that zinc chloride can be recovered from solutions of zinc chloride in water-immiscible organic solvents containing appropriate extractant agents. This is accomplished by contacting the solutions with an aqueous solution of ammonium chloride and ammonia, separating the organic phase, cooling the aqueous phase, and collecting the zinc diammine chloride that precipitates. The zinc diammine chloride was disclosed to be convertible by pyrolysis to anhydrous zinc chloride and ammonia, both of which can be readily recovered. The aqueous solution remaining after removal of the insolubles was disclosed to be recyclable in the system.

SUMMARY OF THE INVENTION

It has now been found that the zinc and ammonia values can be efficiently recovered from aqueous solutions containing zinc chloride or zinc monoammine chloride and ammonium chloride by adding ammonia and separating the solid, insoluble zinc diammine chloride phase that forms from the aqueous ammonium chloride solution phase. The solid zinc diammine chloride phase can be dried and used as is or heated to obtain anhydrous zinc chloride and ammonia. The aqueous ammonium chloride solution phase can be used as is or basified and heated to obtain ammonia. The process has been found to be especially useful for the recovery of the zinc and ammonia values present in the aqueous by-product streams obtained in the zinc reduction of organochlorine compounds.

In particular, a process for recovering zinc and ammonia values from an aqueous solution containing essentially zinc chloride or zinc ammine chloride and ammonium chloride, which process comprises adding sufficient aqueous or anhydrous ammonia to the aqueous solution to achieve a pH of about 5.5 to about 8.5 and, thereafter, removing the precipitate of zinc diammine chloride that forms from the aqueous ammonium chloride liquor and recovering both the precipitate and the liquor has been found.

DETAILED DESCRIPTION OF THE INVENTION

The recovery of zinc values from solutions containing zinc chloride or zinc monoammine chloride and ammonium chloride according to the present invention is accomplished by establishing conditions wherein zinc diammine chloride is formed and is insoluble in the medium. The formation of zinc hydroxy chloride or zinc oxide must be avoided by not allowing the the medium to become too basic and the formation of zinc triammine chloride must be avoided by limiting the amount of ammonia added in the system. Any zinc hydroxy chloride or zinc oxide formed will precipitate and contaminate the zinc diammine chloride product. Zinc triammine chloride is soluble in aqueous media and any zinc in that form cannot readily be recovered as an insoluble solid. In the present invention the desired conditions are achieved by the presence of ammonium chloride in the medium and by control of the pH of the medium to between about 5.5 and about 8.5. The action of ammonium chloride is believed to be attributable to its common ion effect on the equilibria involved in the system, but the operability of the invention is not dependent on the correctness of this belief. Thus, it is believed that the ammonium ion moderates the basicity (pH) of the medium and increases the concentration of free ammonia by its common ion effect on the ammonia-water system:

$$Nh_3 + H_2O \rightleftharpoons NH_4OH \rightleftharpoons N_4^+ + OH^-$$

This increased availability of free ammonia in the system is believed to favor the formation of zinc ammine complexes according to the following equilibria:

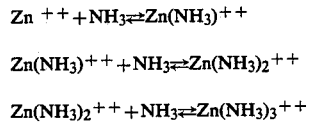

$$Zn^{++} + NH_3 \rightleftharpoons Zn(NH_3)^{++}$$

$$Zn(NH_3)^{++} + NH_3 \rightleftharpoons Zn(NH_3)_2^{++}$$

$$Zn(NH_3)_2^{++} + NH_3 \rightleftharpoons Zn(NH_3)_3^{++}$$

Finally, the chloride ion is believed to decrease the solubility of zinc diammine ion in the system by its common ion effect on the solubility product and, consequently, to improve the efficiency of the recovery of zinc diammine chloride:

$$Zn(NH_3)_2^{++} + 2Cl^- \rightleftharpoons Zn(NH_3)_2Cl_2$$

The presence of some ammonium chloride is essential to the process. The minimum amount believed to be necessary in the final solution from which zinc diammine chloride is separated as a solid is about one mole for every mole of zinc diammine chloride recovered. A 1.5 to 1 mole ratio of ammonium chloride to zinc salt or greater is preferred and an approximately 2 to 1 or greater ratio is more preferred. The upper limit is believed to be very high and determined by factors such as solubility rather than ratio. Not all of the ammonium chloride need be present initially in the solution to be treated. A portion of it can be deliberately added before the addition of ammonia. Further, a portion of it can be made in the media from hydrochloric acid already present or deliberately added and ammonia. In any event, the initial ammonia added will be consumed by any acid present forming ammonium salts. The presence of ammonium salts other than ammonium chloride, such as ammonium acetate, is generally not deleterious to the process and such salts can, in fact, replace some of the ammonium chloride. Ammonium salts having anions that form water insoluble salts with zinc or zinc ammine complexes, however, would probably be unsuitable.

The absolute concentration of ammonium chloride in the system at the time of zinc diammine chloride separation may alter the efficiency of the zinc recovery, but is not believed to be critical. Concentrations of from about 2 percent up to saturated solutions are typical, concentrations of about 10 to about 40 percent are preferred, and concentrations of about 20 to about 35 percent are more preferred.

In many cases the aqueous solutions employed as starting materials in the invention contain appreciable amounts of acid, usually hydrochloric acid, in addition to zinc chloride and ammonium chloride. These acids are converted to ammonium salts when ammonia is added and thus add to the total of ammonium salts in the medium.

Solutions to be subjected to the process that contain mainly zinc monoammine chloride as the zinc salt are often acidified, preferably with hydrochloric acid, before adding ammonia. This procedure, of course, adds more ammonium salt, generally ammonium chloride, to the medium when the ammonia is added.

The zinc in aqueous solutions amenable to the present process is mainly present in the form of zinc chloride or zinc monoammine chloride. Solutions containing from about 2 percent total of these zinc salts up to saturated solutions are typical, solutions containing from about 10 to about 60 percent are preferred, and solutions containing about 20 to about 40 are more preferred.

The aqueous solutions of zinc monoammine chloride and ammonium chloride obtained as by-products in the zinc reduction of organochlorine compounds in the presence of ammonium chloride disclosed in U.S. Pat. No. 4,703,123 are typical of the solutions treated in the process. The byproduct aqueous solutions obtained in the zinc reduction of pentachloropyridine to 2,3,5,6-tetrachloropyridine in the presence of ammonium chloride are especially appropriate. Other aqueous solutions meeting the criteria set out herein can be treated as well. The presence of a water-immiscible solvent containing a zinc extractant agent is not required.

In carrying out the invention, the aqueous solution to be treated is generally placed in a reactor equipped with means for agitation and means for measuring the pH of the medium. In cases where a significant amount of zinc monoammine chloride is present, the solution is typically acidified, generally to a pH of about 3 to about 5 and usually to about 4. Hydrochloric acid is preferably employed. It is sometimes advantageous to treat the solution at this point to remove any organic components. This treatment typically involves extracting the aqueous solution with a water-immiscible solvent, such as toluene, butyl acetate, perchloroethylene or methylene chloride. Such a treatment is particularly helpful when the process is used to treat the by-product streams from processes involving the zinc reduction of organochlorine compounds. Anhydrous or aqueous ammonia is added to the solution with agitation until a pH of about 5.5 to about 8.5 is obtained. It is preferred to secure a pH of about 6 to about 8 and more preferred to secure a pH of about 7 to about 8. A pH of about 7 to about 8 is obtained when the ratio of ammonia to zinc is about 2, which is the theoretical amount of ammonia required. After the zinc diammine chloride has precipitated the solids are separated from the aqueous solution. Any conventional means of separating solids from liquids can be employed; filtration or centrifugation are preferred. The process can be carried out at any convenient temperature between the freezing point and the boiling point of the medium and is preferably carried out at ambient temperatures. Pressure does not appear to be a significant variable, but the process is generally carried out at atmospheric pressure.

The solids obtained in the process contain over 80 percent of the zinc in the system and consist primarily of zinc diammine chloride. Usually over 90 percent of the zinc is recovered, and often over 95 percent recovery is achieved. These solids are contaminated by ammonium chloride only to the extent that the aqueous solution adheres to or otherwise remains associated with the solids after the separation. The zinc diammine chloride precipitate can be purified, if desired, by extraction with methanol. This compound cannot be extracted with water or dilute aqueous ammonia as it is unstable in these media. The solids can be dried by conventional means to obtain a dry product that generally consists of zinc diammine chloride of greater than about 90 percent purity. This dry product can be used for many applications. It can also be converted to anhydrous zinc chloride and ammonia by heating to about 300° C. to about 500° C. to decompose the zinc diammine chloride complex as described in U.S. Pat. No. 4,500,498. Anhydrous zinc chloride is retained as a residue and the ammonia vaporizes and can be recovered by conventional means, such as by condensation.

The aqueous liquor from the separation contains ammonium chloride. This liquor can be basified to a pH of about 10 or greater with an alkali or alkaline earth metal hydroxide, oxide, or carbonate and heated to liberate ammonia, which can be collected by conventional means, such as by condensation. It can also be used as is for most applications for ammonium chloride solutions. In particular, it can be used as the ammonium chloride solution required for the zinc reduction of organochlorine compounds in the presence of ammonium chloride.

The present process is particularly valuable when used in conjunction with processes for the manufacture of 2,3,5,6-tetrachloropyridine by the zinc reduction of pentachloropyridine, as described, for example, in U.S. Pat. No. 4,703,123. The aqueous by-product layer obtained in the reduction can be stripped of any volatile organic solvent, such as acetonitrile, by heating, if desired, and then subjected to the present process. This results in the zinc values in the by-product being recovered as zinc diammine chloride and the ammonia values being recovered as an aqueous solution suitable for recycle back into the reduction process.

The following examples are presented to illustrate the invention and should not be construed as limiting the claims.

EXAMPLE 1

An aqueous solution weighing 325.3 g was analyzed and found to contain about 0.74 mole (101 g, 31 percent) of zinc chloride and about 1.55 moles (82.9 g, 25.5 percent) of ammonium chloride and to have a pH of 4.0. Ammonium hydroxide (85.9 g of a 15.6N solution, 1.49 moles) was added slowly with stirring to a pH of 7.3, and the white granular precipitate that formed was collected by vacuum filtration and dried in a vacuum oven to a constant weight of 123.7 g. Elemental analysis of this precipitate gave 38.0 percent zinc, 42.0 percent chloride, and 16.2 percent nitrogen, which corresponds to 99.0 percent purity zinc diammine chloride. The identification of the product and its purity were confirmed by X-ray diffraction. The precipitate contained 97.0 percent of the zinc and 49.7 percent of the chloride present initially and 96.4 percent of the added ammonia. The filtrate amounted to 274 g and contained 0.48 percent zinc, 18.8 percent chloride, and 7.98 percent nitrogen, which accounts for 98.2 percent of the ammonium chloride initially present.

EXAMPLE 1

An aqueous solution containing 18.0 g (0.132 mole, 30.7 percent) of zinc chloride, 7.44 g (0.139 mole, 12.7 percent) of ammonium chloride, and 10.7 g (0.139 mole, 18.3 percent) of ammonium acetate, weighing 58.6 g and having a pH of 3.9 was prepared in a flask. Aqueous ammonia (15.5 g of 15.6N, 0.268 mole) was added to this dropwise with vigorous agitation. The pH increased to 7.2 The white precipitate that formed was collected by vacuum filtration and dried in a vacuum oven at 100° C. for 2 hours. The wet weight was 23.86 g and the dry weight was 22.18 g. Elemental analysis of this precipitate gave 37.9 percent zinc, 41.9 percent chloride, and 16.2 percent nitrogen, which corresponds to zinc diammine chloride. The dried material was found to amount to 21.6 g, which corresponds to about a 97.4 percent recovery of the zinc. The filtrate amounted to 51.28 g and was found to contain 0.12 g of zinc, 4.79 g of chloride, and 4.87 g of ammonium ion. This is consistent with a solution containing primarily the ammonium chloride and ammonium acetate initially added.

EXAMPLE 3

Pentachloropyridine (190.2 g, 0.757 mole) was placed in a 2-liter titanium Parr reactor and reduced to 2,3,5,6-tetrachloropyridine by adding 52.9 g (0.759 mole) of zinc, 81.0 g (1.51 moles) of ammonium chloride, 260.8 g of water and 816 g of acetonitrile and heating at about 100° C. with agitation for about 165 min. The reaction product was then cooled, transferred to a distillation apparatus, and distilled at atmospheric pressure to remove the acetonitrile, which boils at 78° C. It was then acidified with 75 g (0.76 mole) of concentrated hydrochloric acid, which took the medium to about pH 4, and extracted with 1000 ml of toluene. The extracted aqueous solution was placed in a reactor and 85.94 g (1.518 moles) of concentrated ammonium hydroxide was added dropwise with stirring over a 30 min. period. A precipitate began to form after the addition of about 20 g of the ammonium hydroxide. The final pH was 7.3. After the addition was complete the mixture was stirred for another 30 min. The precipitate was then collected by vacuum filtration, allowed to vacuum dry for about 15 min., and dried in an oven at 115° C. for about 1.5 hr at which time it was at a constant weight of 123.7 g. This precipitate was essentially pure zinc diammine chloride and was found by elemental analysis to contain 97.0 percent of the originally employed zinc and 96.4 percent of the added ammonia. The filtrate amounted to 272 g and was found by elemental analysis to contain 98.2 percent of the originally employed ammonium chloride.

What is claimed is:

1. A process for recovering zinc and ammonia values from an aqueous solution containing essentially zinc chloride or zinc monoammine chloride and ammonium chloride, which process comprises adding sufficient aqueous or anhydrous ammonia to the aqueous solution to achieve a pH of about 6 to about 8 and, thereafter, removing the precipitate of zinc diammine chloride that forms from the aqueous ammonium chloride liquor and recovering both the precipitate and the liquor, so that at least 80 percent of the zinc in the system is recovered in the precipitate.

2. A process according to claim 1 wherein any zinc monoammine chloride present is first converted to zinc chloride and ammonium chloride by adding hydrochloric acid to a pH of about 3 to about 5.

3. A process according to claim 2 wherein the aqueous solution is treated to remove organic components before adding ammonia.

4. A process according to claim 3 wherein the aqueous solution is extracted with an immiscible organic solvent to remove organic components before adding ammonia.

5. A process according to claim 1 wherein the zinc diammine chloride obtained is further dried and heated at about 300° C. to about 500° C. to convert it to anhydrous zinc chloride and ammonia, the anhydrous zinc chloride being recovered by collecting the residue and the ammonia being, optionally, recovered by collecting the vapors emitted.

6. A process according to claim 1 wherein the aqueous liquor is further basified with an alkali or alkaline earth metal oxide, hydroxide, or carbonate and heated to liberate and vaporize the ammonia, and the ammonia is recovered by collecting the vapors.

7. A process according to claim 1 wherein the aqueous liquor is further used as the ammonium chloride source in carrying out the reduction of an organochlorine compound with zinc in the presence of ammonium chloride.

8. A process according to claim 7 wherein the organochlorine compound is pentachloropyridine.

9. A process according to claim 1 wherein the zinc diammine chloride is removed from the aqueous liquor by filtration.

10. A process according to claim 1 wherein the zinc diammine chloride is removed from the aqueous liquor by centrifugation.

11. A process according to claim 1 wherein the aqueous solution containing zinc chloride or zinc monoammine chloride and ammonium chloride is obtained as a by-product from the reduction of an organochlorine compound with zinc in the presence of ammonium chloride.

12. A process according to claim 11 wherein the organochlorine compound is pentachloropyridine.

13. A process according to claim 1 wherein the molar ratio of zinc chloride or zinc monoammine chloride to ammonium chloride is at least 1.5.

14. A process according to claim 1 wherein the molar ratio of zinc chloride or zinc monoammine chloride to ammonium chloride is at least 1.5 and ammonia is added to a pH of between about 6 and about 8.

* * * * *